United States Patent [19]

Terano et al.

[11] Patent Number: 4,743,614

[45] Date of Patent: May 10, 1988

[54] AMINO ACID DERIVATIVES AND PROCESSES FOR PREPARATION THEREOF

[75] Inventors: Hiroshi Terano, Ibaraki; Yasuhisa Tsurumi, Osaka; Hiroyuki Setoi; Masashi Hashimoto, both of Ibaraki; Masanobu Kohsaka, Sakai, all of Japan

[73] Assignee: Fujisawa Pharmaceutical Co., Ltd., Osaka, Japan

[21] Appl. No.: 859,587

[22] Filed: Mar. 4, 1986

[30] Foreign Application Priority Data

Mar. 4, 1985 [GB] United Kingdom ............... 8505481
Aug. 22, 1985 [GB] United Kingdom ............... 8521016
Nov. 18, 1985 [GB] United Kingdom ............... 8528367

[51] Int. Cl.$^4$ ............... A61K 31/165; A61K 31/195; A61K 31/405; A61K 31/415
[52] U.S. Cl. ............................ 514/400; 514/415; 514/468; 514/478; 514/615; 548/344; 548/495; 562/448; 562/561; 564/161; 564/168; 564/192; 564/193
[58] Field of Search ............... 548/353, 344, 495; 530/311; 514/400, 415, 468, 478, 615; 562/448, 561; 564/161, 168, 192, 193

[56] References Cited

U.S. PATENT DOCUMENTS 4,137,416 1/1979 Panzer et al. ............... 548/353
4,145,337 3/1979 Dairman et al. ............ 530/311

FOREIGN PATENT DOCUMENTS 0019411 11/1980 European Pat. Off. .
0091594 10/1983 European Pat. Off. .

3219113A1 11/1983 Fed. Rep. of Germany .

OTHER PUBLICATIONS

Chem. Abstr. vol. 101, (1984) 7605.
Bull. of the Chem. Soc. of Japan 43, 786–789 (1970).
Bull. Chem. Soc. Jpn. 53, 3601–4 (1980).
Chem. Abstr. vol. 95, (1981) 62696.
Chem. Abstr. vol. 100, (1984) 68735.
Chem. Abstr. vol. 102, (1985) 221819.
Chem. Abstr. vol. 87, (1977) 201349.

Primary Examiner—Delbert R. Phillips
Attorney, Agent, or Firm—Oblon, Fisher, Spivak, McClelland & Maier

[57] ABSTRACT

Novel compounds of the following formula have restorative pharmacological activities in immuno-deficient hosts,

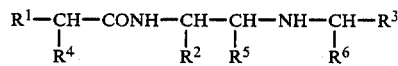

wherein
$R^1$ is amino or a protected amino group,
$R^2$ is hydrogen, carboxy or a protected carboxy group,
$R^3$ is hydrogen, carboxy or a protected carboxy group,
$R^4$ is lower alkyl, amino(lower)alkyl, protected amino(lower)alkyl, carbamoyl(lower)alkyl or protected carbamoyl(lower)alkyl,
$R^5$ is hydrogen or lower alkyl, and
$R^6$ is hydrogen, hydroxyphenyl(lower)alkyl, imidazolyl(lower)alkyl or indolyl(lower)alkyl.

9 Claims, No Drawings

AMINO ACID DERIVATIVES AND PROCESSES FOR PREPARATION THEREOF

The present invention relates to novel amino acid derivatives and pharmaceutically acceptable salts thereof. More particularly, it relates to novel amino acid derivatives and pharmaceutically acceptable salts thereof which have pharmacological activities such as restorative effect on suppressed colony forming abilities of bone marrow cells in immunodeficient hosts, restorative effect on suppressed antibody forming abilities in immunodeficient hosts, inhibitory activity for tumor metastasis or the like, to processes for preparation thereof, to pharmaceutical composition comprising the same.

Accordingly, one object of this invention is to provide novel amino acid derivatives and pharmaceutically acceptable salts thereof.

Another object of this invention is to provide processes for preparation of said amino acid derivatives and pharmaceutically acceptable salts thereof, comprising synthetic processes for preparation of the same and fermentation processes for production of one specific compound in those compounds by culturing a strain belonging to the genus *Discosia* in a nutrient medium.

The object compounds of the present invention can be represented by the following formula (I).

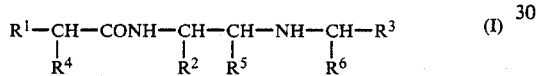

wherein
- $R^1$ is hydrogen, amino or a protected amino group,
- $R^2$ is hydrogen, carboxy or a protected carboxy group,
- $R^3$ is hydrogen, carboxy or a protected carboxy group,
- $R^4$ is lower alkyl, amino (lower)alkyl, protected amino(lower)alkyl, carbamoyl(lower)alkyl or protected carbomoyl(lower, alkyl,
- $R^5$ is hydrogen or lower alkyl, and
- $R^6$ is hydrogen, ar (lower) alkyl which may have suitable substituent(s) or heterocyclic(lower) alkyl.

According to the present invention, the new amino acid dreivatives (I) can be prepared by various processes.

[Production by synthetic process]

Process 1

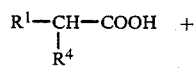

(II)

or its reactive derivative
at the carboxy group
or a salt thereof

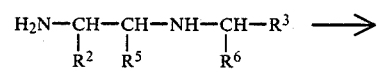

(IIIa)

or its reactive derivative
at the amino group
or a salt thereof

-continued

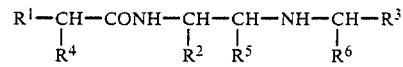

(I)

or a salt thereof

Process 2

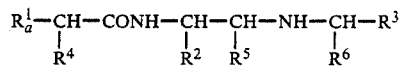

(Ia)

or a salt thereof

↓ Elimination of the amino protective group

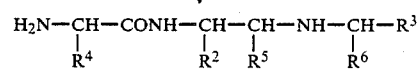

(Ib)

or a salt thereof

Process 3

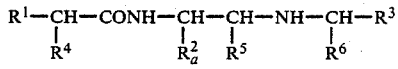

(Ic)

or a salt thereof

↓ Elimination of the carboxy protective group

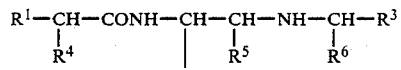

(Id)

or a salt thereof

Process 4

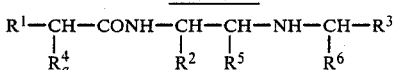

(Ie)

or a salt thereof

↓ Elimination of the carbamoyl protective group

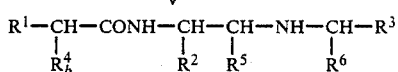

(If)

or a salt thereof wherein
- $R^1$, $R^2$, $R^3$, $R^4$, $R^5$ and $R^6$ are each as defined above,
- $R_a^1$ is a protected amino group,
- $R_a^2$ is a protected carboxy group,
- $R_a^4$ is protected carbamoyl(lower)alkyl, and
- $R_b^4$ is carbamoyyl(lower)alkyl.

The starting compound (IIIa) can be prepared by the following Processes.

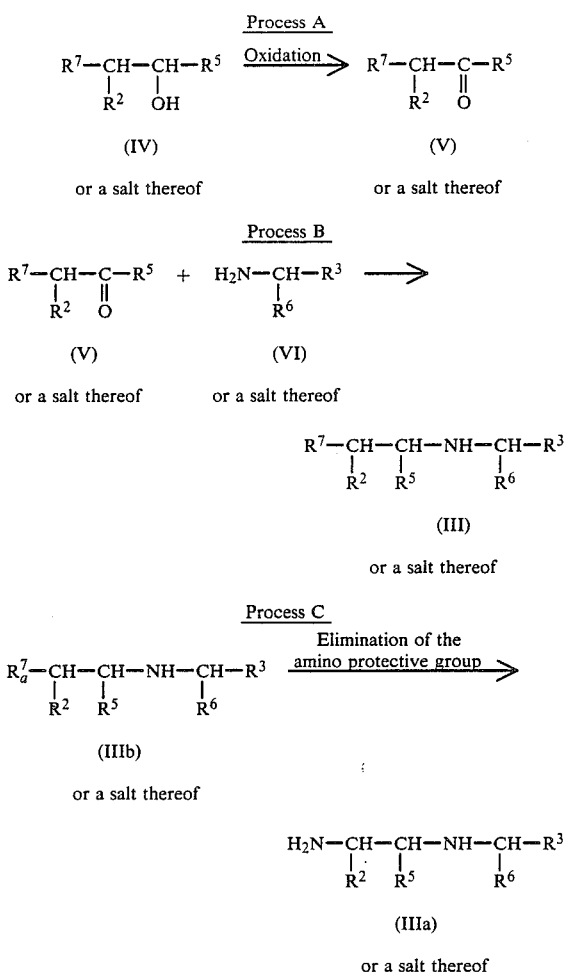

wherein
R$^2$, R$^3$, R$^5$ and R$^6$ are each as defined above,
R$^7$ is amino or a portected amino group, and
R$_a^7$ is a protected amino group.

The processes for preparing the object compounds of the present invention are explained in detail in the following.

Process 1

The compound (I) or a salt thereof can be prepared by reacting the compound (II) or its reactive derivative at the carboxy group or a salt thereof with the compound (IIIa) or its reactive derivative at the amino group or a salt thereof.

Suitable reactive derivative at the amino group of the compound (IIIa) may include Schiff's base type imino or its tautomeric enamine type isomer formed by the reaction of the compound (IIIa) with a carbonyl compound such as aldehyde, ketone or the like; a silyl derivative formed by the reaction of the compound (IIIa) with a silyl compound such as N,O-bis(trimethylsilyl)acetaide, N-trimethylsilylacetamide, bis(trimethylsilyl)urea or the like, a derivative formed by reaction of the compound (IIIa) with phosphorus trichloride or phosgene, and the like.

Suitable salts of the compounds (II) and (IIIa) can be referred to the ones as exemplified for the compound (I).

Suitable reactive derioetive at the carboxy group of the compound (II) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid etc.), dialkylphosphorous acid, sulfurous acid, thiosulfuric acid, lower alkanesulfonic acid (e.g., methanesulfonic acid, ethanesulfonic acid etc.), sulfuric acid, alkylcarbonic acid, aliphatic carboxylic acid (e.g., pivalic acid, pentanoic acid, isopentanoic acid, 2-ethylbutyric acid or trichloroacetic acid etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e g., cyanomethyl ester, methoxymethyl ester, dimethyliminomethyl [(CH$_3$)$_2$N$^+$==CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (II) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (II) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; phosphorus trichloride; thionyl chloride; oxalyl chloride; triphenylphosphine; 2-ethyl-7-hydroxybenzisoxazolium salt; 2-ethyl-5- (m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like. The reaction temperature is not critical, and the reaction is usually carried out under cooling or at ambient temperature.

Process 2

The compound (Ib) or a salt thereof can be prepared by subjecting the compound (Ia) or a salt thereof to elimination reaction of the amino protective group.

Suitable salts of the compounds (Ia) and (Ib) can be referred to the ones as exemplified for the compound (I).

The elimination reaction is carried out in accordance with a conventional method such as hydrolysis; reduction; a method treating the compound (Ia) wherein $R_a{}^1$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like.

Suitable acid includes an organic, inorganic acid or Lewis acid such as formic acid, trifluoroacetic acid, benzenesulfonic acid, p-toluenesulfonic acid, hydrochloric acid, hydrobromic acid, boron trihalide (e.g., boron trifluoride, boron tribromide, etc.), and the like.

The acids can be selected according to the kind of the protective group to be eliminated. When the elimination reaction is conducted with an acid, it can be carried out in the presence or absence of a solvent. Suitable solvent includes water, a conventional organic solvent or a mixture thereof The elimination reaction using trifluoroacetic acid may be carried out in the presence of anisole The hydrolysis using hydrazine is commonly applied for eliminating a phthaloyl, succinyl type aminoprotective group.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g disodium hydrogen phosphate, dipotassium hydrogen phosphate, etc.), or the like, and an organic base such as trialkylamine (e.g. trimethyladine, triethyladine, etc.), picoline, N-methylpyrrolidine, N-methylmorpholine, 1,5diazabicyclo[4.3.0]non-5-ene, 1,4-diazabicyclo[2.2.2]-octane, 1,5-diazabicyclo[5.4.0]undecene-5 or the like. The hydrolysis using a base is often carried out in water or a hydrophilic organic solvent or a mixed solvent thereof.

The reductive elimination is generally applied for eliminating the protective group, for example, haloalkoxycarbonyl (e.g. trichloroethoxycarbonyl, etc.), substituted or unsubstituted aralkoxy carbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on carbon and the like.

Among the protective group, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the protective group for the amino group and the elimination method as mentioned above, and the reaction is preferably carried out under a mild condition such as under cooling or at slightly elevated temperature.

The present invention includes, within its scope, the cases that the protected amino(lower)alkyl and/or protected carbamoyl(lower)alkyl in $R^4$ are transformed into the amino(lower)alkyl and/or carbamoyl(lower)alkyl in the course of the elimination reaction as mentioned above or in the post-treatment of the reaction mixture or reaction product.

Process 3

The compound (Id) or a salt thereof can be prepared by subjecting the compound (Ic) or a salt thereof to elimination reaction of the carboxy protective group.

Suitable salts of the compounds (Ic) and (Id) can be referred to the ones as exemplified for the compound (I).

The present reaction is carried out in accordance with a conventional method such as hydrolysis, reduction or the like.

In case that the protective group is an ester, the protective group can be eliminated by hydrolysis Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4.3.0]-none-5-ene, 1,4-diazabicyclo[2.2.2]octane, 1,8-diazabicyclo[5.4.0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like.

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a solvent such as water, alcohol (e.g. methanol, ethanol, etc.), N,N-dimethylformamide, tetrahydrofuran, a mixture thereof or any other solvent which does not adversely affect the reaction. Additionally, in case that the abovementioned acids to be used in chemical reduction are in liquid, they can also be used as a solvent.

The reaction temperature of this reduction is not critical and the reaction is usually carried out under cooling to warming.

Process 4

The compound (If) or a salt thereof can be prepared by subjecting the compound (Ie) or a salt thereof to elimination reaction of the carbamoyl protective group.

Suitable salts of the compounds (Ie) and (If) can be referred to the ones as exemplified for the compound (I).

The present elimination reaction can be carried out in a similar manner to that of Process 2.

The processes for preparing the starting compound are explained in detail in the following.

Process A

The compound (V) or a salt thereof can be prepared by subjecting the compound (IV) or a salt thereof to oxidation reaction. Suitable salts of the compounds (IV) and (V) can be referred to the ones as exemplified for the compound (I). The oxidation method applicable for this reaction may include, for example, oxidation with a combination of dimethylsulfoxide, N,N'-dicyclohexyl-carbodiimide and acid (e.g. orthophosphoric acid, trifluoroacetic acid, etc.), oxidation with chromic anhydride-pyridine complex, and the like.

This reaction is usually carried out in a solvent such as alcohol [e.g. methanol, ethanol, etc.]methylene chloride, benzene, N,N-dimethylformamide, tetrahydrofuran, diethyl ether or any other solvent which does not adversely affect the reaction.

The reaction temperature is not critical and the reaction is usually carried out under cooling to heating.

Process B

The compound (III) or a salt thereof can be prepared by reacting the compound (V) or a salt thereof with the compound (VI) or a salt thereof and then by subjecting the resultant compound to reduction reaction.

Suitable salts of the compound (III) and (VI) can be referred to the ones as exemplified for the compound (I). The reduction method applicable for this reaction may include, for example, reduction with a borane derivative (e.g. sodium borohydride, sodium cyanoborohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on charcoal and the like.

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction temperature is not critical and the reaction is usually carried out under cooling to heating.

Process C

The compound (IIIa) or a salt thereof can be prepared by subjecting the compound (IIIb) or a salt thereof to elimination reaction of the amino protective group. Suitable salt of the compound (IIIb) can be referred to the one as exemplified for the compound (I).

The present elimination reaction can be carried out according to substantially the same manner as that of Process 2.

The present reaction includes, within its scope, the cases that the protected carboxy group for $R^2$ and/or $R^3$ is transformed into the free carboxy group in the course of the elimination reaction as mentioned above or in the post-treatment of the reaction mixture or reaction product.

[Production by Fermentation]

Among the object compounds of this invention, one specific compound (hereinafter referred to as FR-900490) can be produced by fermentation. And, said FR-900490 has the following physicochemical properties:

(a) Appearance : White powder
(b) Decomposition point : 172°–174° C.
(c) Optical rotation : $[\alpha]_D^{23} = +17.5°$ (C=1.0, $H_2O$)
(d) Molecular weight : 370 [SIMS : m/z 371 (M+1]
(e) Elemental analysis (%) : C 40.55; H 6.19; N 20.45

(f) UV absorption spectrum : End absorption (in $H_2O$)
(g) IR absorption spectrum : $\nu_{Max}^{KBr}$ 3400 2920 1680 1620 1390 1100 $cm^{-1}$
(h) $^1H$ NMR absorption spectrum : ($D_2O$) δppm : 8.01 (1H, s), 7.17 (1H, s), 4.44 (1H, d, J=5.0Hz), 4.24 (1H, dd, J=4.95Hz and 7.91Hz), 3.99 (1H, dd, J=5.3Hz and 8.2Hz), 3.55 (1H, m), 3.30 (1H, dd, J=5.3Hz and 15.0Hz), 3.16 (1H, dd, J=8.2Hz and 15.0Hz), 2.96 (1H, dd, J=4.95Hz and 16.5Hz), 2.83 (1H, dd, J=7.91Hz and 16.5Hz), 1.16 (3H, d, J=6.6Hz)

(i) $^{13}$C NMR absorption spectrum : (D$_2$O) δppm : 174.3 (s), 174.3 (s), 174.2 (s), 171.1 (s), 136.4 (d), 131.7 (s), 117.5 (d), 60.2 (d), 56.1 (d), 53.6 (d), 51.0 (d), 36.7 (t), 28.3 (t), 12.5 (q)

(j) Solubility :
  Soluble : Water
  Sparingly soluble : Methanol, ethanol
  Insoluble : Ethyl acetate, chloroform, acetone (k) Color reaction :
  Positive : Ninhydrin reaction, reaction with iodine vapor, reaction with cerium sulfate, reaction with potassium permanganate
  Negative : Ferric chloride reaction, reaction with Dragendorff reagent, Molisch reaction, phosphomolybdic acid reaction (l) Property of substance : Amphoteric substance (m) Thin layer chromatography (silica gel plate) :

| Solvent | Rf value |
| --- | --- |
| n-butyl alcohol:acetic acid:water (2:1:2) | 0.27 |
| n-butyl alcohol:ethanol:chloroform: 28% ammonia water (2:2:1:2) | 0.22 |
| 70% aqueous isopropyl alcohol (containing 0.28% ammonia) | 0.25 |

The FR-900490 can be prepared by culturing a FR-900490-producing strain belonging to the genus Discosia such as Discosia sp. F-11809 and the like in a nutrient medium and recovering the FR-900490 from the cultured broth.

Among a FR-900490-producing strain belonging to the genus Discosia, Discosia sp. F-11809 was newly isolated from a soil sample collected at the foot of Mt. Takao, Kyoto Prefecture, Japan by the present inventors.

A lyophilized sample of the newly isolated Discosia sp. F-11809 was deposited with Fermentation Research Institute, Agency of Industrial Science and Technology, Yatabe-cho higashi No. 1-1-3, Tsukuba-gun, Ibaraki-ken, Japan, under the number FERM P-8070 on Jan. 25, 1985, and then converted to Budapest Treaty route of the same depository on Feb. 8, 1986 under the new deposit number of FERM BP-982.

It is to be understood that the production of the new compound FR-900490 is not limited to the use of the particular organism described herein, which is given for illustrative purpose only. This invention also includes the use of any mutants which are capable of producing the FR-900490 including natural mutants as well as artificial mutants which can be produced from the described organism by conventional means, such as X-rays, ultra-violet radiation, treatment with N-methyl-N'-nitro-N-nitrosoguanidine, 2-aminopurine and the like.

Discosia sp. F-11809 has the following morphological, cultural and physiological characteristics.

While no teleomorph developed on various culture media, the hyphal conidiomata were abundantly observed on corn meal agar and many pycnidia were formed on a leaf segment inoculated with conidia of the strain F-11809. The conidiogenesis is holoblastic, and conidia are solitary.

The conidiomata (pycnidia) are immersed, separate or aggregated, flattened stromatic, papillate, 200–400 μm in diameter and 40–80 μm high. The papillae possessing one ostiole are 20–50 μm in diameter, and the pycnidial walls consist of several layers of dark brown cells. The conidiophores are absent. The conidiogenous cells, formed at the lower layer of inner pycnidial walls, are obpyriform to lageniform, 7–10 μm long and 4–5 μm thick tapering to 2 μm thick at the apices. The conidia are subhyaline, smooth, cylindrical to allantoid, 3-septate, truncate at the base, 15–22(–25) μm long and 2.5–3.5 μm thick. Their apical and basal cells have a setula near the septum respectively. The setulae are unbranched, filiform, 12–20(–30) μm long and 0.5–1 μm thick.

The vegetative hyphae are septate, subhyaline to dark brown, smooth and branched. The hyphal cells are cylindrical or doliiform, and 1.5–4 μm thick. The chlamydospores are absent, but stromatic hyphal masses composed of irregular cells are formed on some media.

Colonies on malt extract agar spread broadly, attaining 8.0 cm in diameter after 2 weeks at 25° C. The colony surface is plane, felty, wrinkly at the center, growing circularly and light olive gray to olive gray. The conidial structures are not produced. The reverse is olivaceous black or dark olive. Cultures on corn meal agar reach 7.5 cm in diameter under the same conditions. The surface is plane, thin, felty and grayish yellow brown to brownish gray. The reverse is the same. The conidia are formed in abundance at many positions, and the dark brown hyphal masses are produced in or on agar media.

The strain F-11809 can grow at the temperature in the range from 2 to 34° C. with the growth optimum at 24 to 31° C. These temperatural data were determined using a temperature gradient incubator (Toyo Kagaku Sangyo Co., Ltd.) on potato dextrose agar. This strain can grow at pH 3 to 9, and has a growth optimum at pH 6 to 7 in YM broth medium (Difco).

From the above mentioned characteristics, it seemed that the strain F-11809 belonged to the hyphomycete genus Discosia Libert. The genus was divided into five described species plus three other species delimited on the basis of conidial characters by Subramanian and Chandra-Reddy (Kavaka, 2:57-89, 1974).

According to their criteria, our strain resembled Discosia strobilina Libert, but its conidial characteristics (i.e. position of the conidial appendages etc.) were often changed by cultural conditions. Then, we determined the strain F-11809 as one strain of the genus Discosia, and named it Discosia sp. F-11809.

In general, FR-900490 can be produced by culturing a FR-900490-producing strain in a nutrient medium containing assimilable sources of carbon and of nitrogen, preferably under aerobic conditions (e.g. shaking culture, submerged culture, etc.).

The preferred sources of carbon in the nutrient medium are carbohydrate such as glucose, fructose, glycerin and starch. Other sources which may be included are lactose, arabinose, xylose, dextrin, molasses and the like.

The preferred sources of nitrogen are yeast extract, peptone, gluten meal, cotton seed meal soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR-900490. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900490. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR-900490.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably 25–30° C., for a period of 50 hours to 100 hours, which may be varied according to the fermentation conditions and scale.

Thus produced FR-900490 can be recovered from the culture medium by conventional means which are commonly used for the recovery of other fermentation products such as antibiotics.

In general, most of the FR-900490 produced are found in the culture filtrate, and accordingly FR-900490 can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. active carbon, silicic acid, silica gel, cellulose, alumina), crystallization, recrystallization and the like.

From the analysis of the above physical and chemical properties, and the result of further investigation for identification of chemical structure, the chemical structure of the FR-900490 has been identified and assigned as follows.

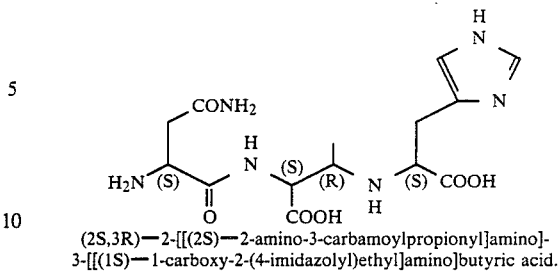

(2S,3R)—2-[[(2S)—2-amino-3-carbamoylpropionyl]amino]-3-[[(1S)—1-carboxy-2-(4-imidazolyl)ethyl]amino]butyric acid.

Suitable pharmaceutically acceptable salts of the object compounds (I) are conventional non-toxic salt and include a metal salt such as alkali metal salt (e.g. sodium salt, potassium salt, etc.) and an alkaline earth metal salt (e.g. calcuim salt, magnesium salt, etc.), an ammonium salt, an organic base salt (e.g. trimethylamine salt, triethylamine salt, pyridine salt, picoline salt, sicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atoms, unless otherwise indicated.

Suitable "protected amino" and "protected amino moiety" in the term "protected amino(lower)alkyl" may include an acylavmino or an amino group substituted by a conventional protective group such as ar(-lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Suitable "protected carboxy" may include an esterified carboxy and the like.

Suitable examples of the ester moiety in said esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymeth-yl ester, butyryloxymethyl ester, valeryloxymethyl ester, pivaloyloxymethy-1 ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)propionyloxyethyl ester, 1(or 2 or 3)-propionyloxypropyl ester, 1(or 2)-butyryloxyethyl ester, 1(or 2)isobutyryloxyethyl ester, 1(or 2)-pivaloyloxyethyl ester, 1(or 2)-hexanoyloxyethyl ester, isobutyryloxymethyl ester, 2-ethylbutyrylox-ymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), or phthalidylidene(lower)alkyl ester;

lower alkenyl ester (e.g. vinyl ester, allyl ester, etc.); lower alkynyl ester (e.g. ethynyl ester, propynyl ester, etc.);

ar(lower)alkyl ester [e.g., mono(or di or tri)phenyl(lower)alkyl ester, etc.] which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di- tert- butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Suitable "lower alkyl" and "lower alkyl moiety" in the terms "amino(lower)alkyl", "protected amino(lower)alkyl", "carbamoyl(lower)alkyl", "protected carbamoyl(lower)alkyl", "ar(lower)alkyl which may have suitable substituent(s)" and "heterocyclic(lower)alkyl" may include straight or branched saturated aliphatic hydrocarbon residue such as methyl, ethyl, propyl, isopropyl, butyl, isobutyl, tert-butyl, pentyl, neopentyl, tert-pentyl, hexyl, and the like.

Suitable protective group of carbamoyl group may include ar(lower)alkyl ester [e.g., mono(or di or tri)-phenyl(lower)alkyl ester, etc.] which may have suitable substituents [e.g., 2,4-dimethoxybenzyl ester, bis(methoxyphenyl)methyl ester, etc.), and the like.

Suitable "aryl moiety" in the term "ar(lower)alkyl which may have suitable substituent(s)" may include phenyl, naphtyl and the like.

Suitable substituent in the term "ar(lower)alkyl which may have suitable substituent(s)" may include hydroxy and the like.

Suitable "heterocyclic moiety" in the term "heterocyclic(lower)alkyl" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; saturated 3 to 6-membered heteromonocyclic group containing 1 to 4 nitrogen atoms (e.g., pyrrolidinyl, imidazolidinyl, piperidino, piperazinyl, etc.); unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 6-membered heteromonocyclic group containing 1 to 2 oxygen atoms and 1 to 3 nitrogen atoms (e.g., morpholinyl, etc.);

unsaturated condensed heterocyclic group containing 1 to 2 oxygen atoms and 1 to 3 nitrogen atoms (e.g., benzoxazolyl, benzoxadiazolyl, etc.);

unsaturated 3 to 6-membered heteromonocyclic group containing 1 to 2 sulfur atoms and 1 to 3 nitrogen atoms, for example, thiazolyl, thiadiazolyl (e.g., 1,2,4thiadiazolyl, 1,3,4-thiadiazolyl, 1,2,5-thiadiazolyl, etc.), etc.;

saturated 3 to 6-membered heteromonocyclic group containing 1 to 2 sulfur atoms and 1 to 3 nitrogen atoms (e.g., thiazolidinyl, etc.);

unsaturated condensed heterocyclic group containing 1 to 2 sulfur atoms and 1 to 3 nitrogen atoms (e.g., benzothiazolyl, benzothiadiazolyl, etc.) and the like.

Preferrable embodiments of the object compounds (I) are as follows.

Preferred embodiment of $R^1$ is hydrogen, amino or a protected amino group [more preferably acylamino, most preferably lower alkoxycarbonylamino, ar(lower)alkoxycarbonylamino or lower alkanoylamino], $R^2$ is hydrogen, carboxy or a protected carboxy group [more preferably esterified carboxy group, most preferably lower alkoxycarbonyl], $R^3$ is hydrogen or carboxy, $R^4$ is lower alkyl, amino(lower)alkyl, protected amino(lower)alkyl [more preferably acylamino(lower)alkyl, most preferably ar(lower)alkoxycarbonylamino(lower)alkyl], carbamoyl(lower)alkyl or protected carbamoyl(lower)alkyl [more preferably [bis(4methoxyphenyl)methyl]carbamoyl(lower)alkyl], $R^5$ is hydrogen or lower alkyl, and $R^6$ is hydrogen, hydroxyphenyl(lower)alkyl or heterocyclic(lower)alkyl [more preferably imidazolyl(lower)alkyl or indolyl-(lower)alkyl].

In order to illustrate the usefulness of the object compound (I), some biological properties of the representative compound are illustrated in detail in the following tests.

Test compound (2S,3R)-2-[[(2S)-2-amino-3-carbamoylpropionyl]amino]-[[(1S)-1-carboxy-2-(4-imidazolyl)ethyl]amino]-butyric acid. [FR-900490]

Test 1

Restorative effect on suppressed colony forming abilities of bone marrow cells in immunodeficient hosts:

$BDF_1$ mice (female, 8 weeks aged) were obtained from Shizuoka Agricultural Cooperative Association for Laboratory Animal, Hamamatsu, Japan. The mice were intraperitoneally injected with mitomycin C (1 mg/kg) every day for 2 days and FR-900490 was also administered to mice intraperitoneally every day for 5 days. At 9th day after first administration of mitomycin C, mice were sacrificed and the colony forming abilities of bone marrow cells (CFU-c) were measured. The schedule of the above test is shown below.

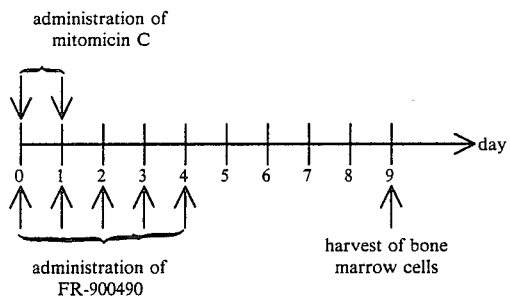

Femoral marrow was harvested from mice by flushing the bone cavity with α-Minimum Essential Medium (α-MEM) supplemented with penicillin G (100 units/ml), streptomycin (100 μg/ml) and 5% fetal bovine serum (FBS). The bone marrow cells were pelleted by centrifugation (500×g, 10 minutes) and resuspended in enriched α-MEM. Mononuclear cells were counted in a hemocytometer and the cells were diluted to $1 \times 10^5$ cells/ml. Then, 1 ml of bone marrow cells, 1 ml of FBS, 2 ml of 2.2% methyl cellulose in α-MEM and 1 ml of L-929 cell conditioned medium were added to a sterilized tube and mixed by use of automatic mixer. One ml of mixture was plated in 35 mm plastic petri dish and incubated for 7 days in a fully humidified atmosphere of 5% $CO_2$ in air. Triplicate plates were prepared for each experiment. Colonies composed of 50 or more cells were scored on an inverted microscope. The result is shown in Table 1.

TABLE 1

| Drug | Dose (mg/kg) | CFU-c (mean ± SE) |
|---|---|---|
| Control (1)* | — | 118 ± 5.3 |
| Control (2)** | — | 20:1 ± 3.19 |
| Control (3)*** | — | 12.6 ± 0.34 |
| FR-900490 | 100 | 57.2 ± 2.51** |
| | 10 | 70.4 ± 6.9** |
| | 1 | 59.3 ± 2.86** |
| | | **P < 0.01 (n = 7–9) |

*Animals for control (1) were administered neither mitomycin C nor FR-900490.
**Animals for control (2) were administered neither mitomycin C nor FR-900490, and L-929 cell conditioned medium was not used for incubation of bone marrow cells.
***Animals for control (3) was not administered FR-900490.

Test 2

Inhibitory activity for tumor metastasis

B-16 Melanoma cells were grown in a Roswel park memorial Institute (RPMI)-1640 medium supplemented with penicillin G (100 units/ml), streptomycin (100 μg/ml) and 10% FBS to subsconfiluency, and the monolayers were rinsed with an aqueous solution of trypsin. Hanks' balanced salt (HBS) solution (Ca-Mg-free) containing the antibiotics described above was added to the monolayers and the monolayer was dislodged by gentle pipetting, and the cells were washed with HBS solution containing the antibiotics described above by centrifugation. The cells were resuspended in HBS solution containing the antibiotics described above and kept at cold temperature. BDF₁ mice (female, 8 weeks aged) were injected intravenously with $2 \times 10^5$ cells of B-16 melanoma in 0.2 ml of HBS solution containing the antibiotics described above. FR-900490 was intraperitoneally administered once a day at one day and two days before and at one day and four days after the injection of B-16 melanoma. At 14th day after injection of B-16 melanoma, the mice were killed, and the lungs were removed, rinsed in distilled water containing heparin and the number of tumor foci was determined by counting the surface colonies under a dissecting microscope.

The schedule of the above test is shown.

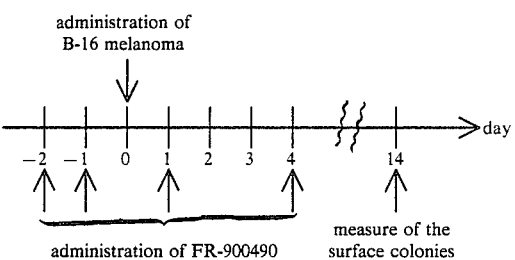

The result is shown in Table 2.

TABLE 2

| Drug | Dose (mg/kg) | No. of colonies on the lung mean ± SE |
|---|---|---|
| Control | — | 257.6 ± 39.7 |
| FR-900490 | 1 | 39.7 ± 6.4** |
| | 10 | 23.4 ± 3.3** |
| | 100 | 77.9 ± 27.4** |
| | | **P < 0.01 (n = 10) |

Test 3

Acute toxicity of the FR-900490

Test on acute toxicity of the FR-900490 in ddY mice (female, 5 weeks aged) by intravenous injection were conducted, and the dead at dose of 1000 mg/kg could not be observed.

Test 4

Restorative Effect on Suppressed Antibody Forming Abilities in Immunodeficient Hosts BDF₁ mice (female, 8 weeks aged) were injected intraperitoneally with Mitomycin C (1 mg/kg) from four days before immunization with $5 \times 10^8$ Sheep Red Blood Cells (SRBC), every day for three days. Test samples also were administered to mice intraperitoneally from four days before immunization, every day for five days. At day 9, mice were sacrificed and the number of direct plaque forming cells per spleen (PFC-SRBC/spleen) was measured by using Cunningham modification method.

The schedule of the above test is shown.

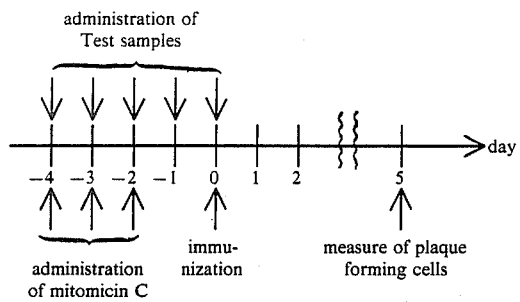

administration of Test samples administration of mitomicin C immunization measure of plaque forming cells The result is shown in Table 3.

TABLE 3

| Test Sample | Dose (mg/kg) | PFC-SRBC/spleen (average number of 5 mice/group) |
| --- | --- | --- |
| Control* (Saline) | — | $14.52 \times 10^4$ |
| Control (Saline) | — | $9.57 \times 10^4$ |
| FR-900490* | 100 | $16.83 \times 10^4$ |
| FR-900490 | 100 | $21.12 \times 10^4$ |
|  | 30 | $16.30 \times 10^4$ |
|  | 10 | $17.49 \times 10^4$ |
|  | 3 | $14.96 \times 10^4$ |

*Animals were not administered mitomycin C.

The pharmaceutical composition of this invention can be used in the form of a pharmaceutical preparation, for example, in solid, semisolid or liquid form, which contains the object compounds, as an active ingredient, in admixture with an organic or inorganic carrier or excipient suitable for external, enteral or paraenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

A dosage of the object compounds are to be varied depending on various factors such as kind of diseases, weight and/or age of a patient, and further the kind of administration route.

The preferred dosage of the object compounds is usually selected from a dose range of 0.1-100 mg/kg/day.

The following Preparations and Examples are given for the purpose of illustrating this invention.

Preparation 1

To a solution of methyl (2S,3R)-3-hydroxy-2-tritylaminobutyrate (1.00 g) in a mixture of benzene (6 ml) and dimethylsulfoxide (6 ml) were successively added pyridine (212 mg), trifluoroacetic acid (152 mg) and N,N'-dicyclohexylcarbodiimide (1.65 g) and the resulting solution was stirred overnight at room temperature. To the mixture were added water (10 ml) and ethyl acetate and the insoluble material was filtered off.

The organic layer was separated and washed successively with water and brine. The solution was dried over magnesium sulfate and chromatographed on a silica gel (25 g) column with a mixture of n-hexane and ethyl acetate (5:1) as an eluent to give methyl (2S)-3-oxo-2-tritylaminobutyrate (563 mg) as a pale yellow oil.

NMR (CDCl$_3$, δ): 1.98 (3H, s), 3.50 (3H, s), 4.17 (1H, s), 7.1–7.6 (15H, m)

Preparation 2

To a mixture of methyl (2S)-3-oxo-2-tritylaminobutyrate (397 mg) and methyl (2S)-2-amino-3-(4-imidazolyl)-propionate dihydrochloride (388 mg) in methanol (10 ml) was added sodium cyanoborohydride (66.7 mg) and the solution was stirred overnight at room temperature. To the reaction mixture was added sodium bicarbonate (400 mg) in water (10 ml) and the resulting aqueous solution was extracted with chloroform (40 ml). The extract was washed with brine, dried over magnesium sulfate and evaporated in vacuo.

The residue was chromatographed on a silica gel (20 g) column with a mixture of chloroform and methanol (50:1) as an eluent to give methyl (2S,3R)-3-[[(1S)-1-methoxycarbonyl-2-(4-imidazolyl)ethyl]amino]2-tritylaminobutyrate (141 mg) as a yellow amorphous powder.

mp: 55°–58° C.

IR (Nujol): 1720, 1195, 1180 cm$^{-1}$

NMR (CDCl$_3$, δ): 0.97 (3H, d, J=6Hz), 2.6–3.1 (3H, m), 3.13 (3H, s), 3.41 (1H, m), 3.58 (1H, m), 3.68 (3H, s), 5.50 (2H, broad), 6.13 (1H, s), 7.1–7.6 (16H, m)

Preparation 3

To a mixture of methyl (2S)-3-oxo-2-tritylaminobutyrate (2.00 g) and methyl (2S)-2-amino-3-(3-indolyl)propionate mono-p-toluenesulfonate (3.13 g) in methanol (30 ml) was added sodium cyanoborohydride (360 mg) and the mixture was stirred for 1 day at room temperature. The mixture was diluted with chloroform and washed successively with water and brine. The organic phase was separated and dried over magnesium sulfate, and the solvent was evaporated in vacuo. The residue was chromatographed on a silica gel (50 g) column and the elution was carried out with a mixture of n-hexane and ethyl acetate (4:1). The object fractions were collected and evaporated in vacuo to give methyl (2S,3R)-3-[[(1S)-1-methoxycarbonyl-2-(3-indolyl)ethyl]amino]-2-tritylaminobutyrate (625 mg) as a pale yellow oil.

NMR (CDCl$_3$, δ): 0.99 (3H, d, J=6Hz), 2.93 (1H, t, 6Hz), 3.06 (3H, s), 3.20 (2H, d, J=6Hz), 3.3–3.6 (1H, m), 3.58 (3H, s), 3.77 (1H, m), 7.1–7.7 (20H, m), 7.96 (1H, m)

Preparation 4

The following compounds were obtained according to similar manners to those of Preparations 2 and 3.

(1) Methyl (2S,3R)-3-[[2-(4-imidazolyl)ethyl]amino]-2-tritylaminobutyrate

NMR (CDCl$_3$, δ): 1.11 (2H, d, J=6Hz), 2.6–3.1 (5H, m), 3.17 (3H, s), 3.48 (1H, m), 6.74 (1H, s), 7.1–7.6 (16H, m)

(2) Methyl (2S,3R)-3-[[(1S)-1-ethoxycarbonyl-2-(4-hydroxyphenyl)ethyl]amino]-2-tritylaminobutyrate NMR (CDCl$_3$, δ): 0.97 (3H, d, J=6Hz), 1.18 (3H, t, J=8Hz), 2.6–3.0 (1H, m), 2.93 (2H, d, J=6Hz), 3.07 (3H, s), 3.29 (1H, m), 3.60 (1H, t, J=6Hz), 4.12 (2H, q, J=8Hz), 6.66 (2H, d, J=8Hz), 7.06 (2H, d, J=8Hz), 7.1–7.6 (15H, m)

(3) Methyl (2S,3R)-3-methoxycarbonylmethylamino2-tritylaminobutyrate

NMR (CDCl$_3$, δ): 1.07 (3H, d, J=6Hz), 3.07 (1H, m), 3.14 (3H, s), 3.37 (2H, s), 3.41 (1H, m), 3.70 (3H, s), 7.1–7.6 (15H, m)

Preparation 5

To a solution of methyl (2S,3R)-3-[[(1S)-1-methoxycarbonyl-2-(4-imidazolyl)ethyl]amino]-2-tritylaminobutyrate (400 mg) in methylene chloride (10 ml) in an ice-salt bath was added dropwise a solution of boron tribromide (952 mg) in methylene chloride (5 ml) and the mixture was stirred overnight at room temperature. The pale yellow powder precipitated during a course of the reaction was collected by filtration, washed with methylene chloride and dissolved in water. The solution was subjected to a column of Dowex 50W x 8 (Trademark, Dow Chemical Company) (20 ml) and eluted with 2.8% aqueous ammonia. The object fractions were evaporated in vacuo and the residue was crystallized from methanol to give (2S,3R)-2-amino-3-[(1S)-1-carboxy-2-(4-imidazolyl)ethyl]amino]butyric acid (55 mg) as a white powder.

mp: 226°–230° C.

IR (Nujol): 1615, 1560, 1405, 1245 cm$^{-1}$

NMR (D$_2$O-NaOD, δ): 0.98 (3H, d, J=6Hz), 2.57 (1H, m), 2.83 (2H, d, J=7Hz), 2.97 (1H, d, J=8Hz), 3.47 (1H, t, J=7Hz), 6.84 (1H, s), 7.53 (1H, s)

Preparation 6

A solution of methyl (2S,3R)-3-[[(1S)-1-methoxycarbonyl-2-(3-indolyl)ethyl]amino]-2-tritylaminobutyrate (600 mg) in a mixture of methanol (10 ml) and 1N hydrochloric acid (2 ml) was stirred for 1 hour at room temperature and methanol was evaporated in vacuo. The residual aqueous solution was washed with chloroform and diluted with water (15 ml). To the solution was added sodium hydroxide (500 mg) and the mixture was stirred overnight at room temperature. The mixture was adjusted to pH 3 with 1N hydrochloric acid and the solution was subjected to a column of Dowex 50W x 8 (H$^+$, 20 ml). The column was washed with water and the elution was carried out with 1.4% aqueous ammonia. The object fractions were collected and lyophilized to give (2S,3R)-2-amino-3-[[(1S)-1-carboxy-2-(3-indolyl)ethyl]amino]butyric acid (260 mg) as a white powder.

mp: 159°–163° C.

NMR (D$_2$O, δ): 1.00 (3H, d, J=6Hz), 3.20 (1H, m), 3.4–3.8 (1H, m), 3.8–4.3 (2H, m), 7.2–7.4 (3H, m), 7.57 (1H, m), 7.76 (1H, m)

Mass (SIMS): m/z 306 (M$^+$+1)

Preparation 7

Methyl (2S,3R)-3-[[(1S)-1-ethoxycarbonyl-2-(4-hydroxyphenyl)ethyl]amino]-2-tritylaminobutyrate (1.13 g) was treated according to a similar manner to that of Preparation 6 to give (2S,3R)-2-amino-3-[[(1S)-1-carboxy-2-(4-hydroxyphenyl)ethyl]amino]butyric acid (375 mg).

NMR (D$_2$O, δ): 0.99 (3H, d, J=6Hz), 2.61 (1H, m), 2.72 (2H, d, J=7Hz), 2.93 (1H, d, J=8Hz), 3.41 (1H, dd, J=6, 7Hz), 6.54 (2H, d, J=8Hz), 7.00 (2H, d, J=8Hz)

Preparation 8

The following compound was obtained according to a similar manner to that of Preparation 6.

(2S,3R)-2-Amino-3-carboxymethylaminobutyric acid

NMR (D$_2$O, δ): 1.50 (3H, d, J=6Hz), 3.5–4.0 (1H, m), 3.76 (2H, s), 4.16 (1H, m)

Preparation 9

(1) A solution of methyl (2S,3S)-3-methyl-1-tosyl-2-aziridinecarboxylate (2.45 g) in a mixture of methanol (9.5 ml) and 1N aqueous sodium hydroxide (9.1 ml) was stirred for 30 minutes at room temperature and to the mixture were added D-histidine monohydrochloride (5.23 g) and sodium hydroxide (2.55 g). The solution was refluxed for 5 hours and the solvent was evaporated in vacuo. The residue was dissolved in water and adjusted to pH 5 with 1N hydrochloric acid. The solution was subjected to a column of Diaion HP-20" (Trademark: prepared by Mitsubishi Chemical Industries) (100 ml) and the column was washed with water. The elution was carried out with a mixture of methanol and water (1:1) to give mixed products (2.47 g) of (2S,3R)-3-[[(1R)-1-carboxyl-carboxy-2-(4-imidazolyl)ethyl-]amino]-2-tosylaminobutyric acid and (2S,3R)-2-[[(1R)-1-carboxy-2-(4-imidazolyl)ethyl]amino]-3-tosylaminobutyric acid.

(2) To a mixture of the mixed products 2.47 g) obtained in Preparation 9(1) and liquid ammonia (30 ml) was added sodium (1.25 g) at −78° C. and the mixture was stirred for 5 hours at the same temperature. To the mixture was added ammonium chloride until the blue color disappeared and ammonia was evaporated at room temperature. The residue was diluted with water and adjusted to pH 4 with 1N hydrochloric acid. The solution was subjected to a column of Dowex 50W x 8 (30 ml) and the column was washed with water. Next, the elution was carried out with 2.8% aqueous ammonia and the eluent was evaporated in vacuo. The residue was dissolved in pyridine-acetic acid buffer (0.01M, pH 4.5) and subjected to a column of Whatman CM52 (300 ml). The column was washed with the same buffer and the elution was carried out with pyridine-acetic acid buffer (0.01–0.3M, pH 4.5). The fractions containing the object compound were collected and evaporated in vacuo and the residue was solidified with methanol to give (2S,3R)-2-amino-3-[[(1R)-1-carboxy-2-(4-imidazolyl)ethyl]amino]butyric acid (584 mg) as a yellow brown powder.

mp: 168°–171° C. (dec.)

NMR (D$_2$O, δ): 1.25 (3H, d, J=7Hz), 2.9–3.6 (3H, m), 3.03 (2H, d, J=6Hz), 3.68 (1H, d, J=3Hz), 7.26 (1H, s), 8.46 (1H, s)

Mass (SIMS): m/z 257 (M$^+$+1)

EXAMPLE 1

To a mixture of (2S,3R)-2-amino-3-[[(1S)-1-carboxy-2-(4-imidazolyl)ethyl]amino]butyric acid (51 mg) and triethylamine (0.14 ml) in a mixture of water (1 ml) and dioxane (1 ml) was added p-nitrophenyl t-butoxycarbonyl-L-asparaginate (200 mg) and the mixture was stirred at room temperature. After 15 hours, an additional 200 mg of p-nitrophenyl t-butoxycarbonyl-L-asparaginate and triethylamine (0.14 ml) were added and the mixture was stirred at room temperature for 4 hours. Further, 200 mg of p-nitrophenyl t-butoxycarbonyl-L-asparaginate and triethylamine (0.14 ml) were added and the mixture was stirred for 4 hours at the same temperature.

The reaction mixture was diluted with water (5 ml), neutralized with 1N hydrochloric acid and washed with ethyl acetate (10 ml), and the aqueous phase was evaporated in vacuo.

The residue was dissolved in 75% aqueous trifluoroacetic acid (5 ml and the solution was stirred for 3 hours at room temperature. After evaporation of the solvent in vacuo, the residue was dissolved in water (5 ml) and the solution was adjusted to pH 7 with 1N aqueous sodium hydroxide. The solvent was evaporated in vacuo and the residue was dissolved in pyridine-acetic acid buffer (0.01M, pH 5.0). The solution was applied to a column of Whatman CM52 (Trademark, Whatman) (50 ml) and the column was washed with the same buffer (70 ml). The elution was carried out with pyridine-acetic acid buffer (0.01–0.1M, pH 5.0). The fractions containing the object compound were collected and the solvent was evaporated in vacuo. The residue was subjected to a column of Amberlite IRA400 (Trademark, Rohm & Haas) (OH−, 10 ml) and the column was washed with water (50 ml), and the elution was carried out with 4% aqueous acetic acid (20 ml). The solvent was evaporated in vacuo and the residue was chromatographed on a silica gel (3 g) column with a mixture of chloroform, methanol and conc. aqueous ammonia (5:3:1) as an eluent to give (2S,3R)-2-[[(2S)-2-amino-3-carbamoylpropionyl]amino]-3-[[(1S)-1-carboxy-2-(4-imidazolyl)ethyl]amino]butyric acid (19.8 mg).

NMR (D$_2$O-NaOD, δ): 1.14 (3H, d, J=7Hz), 2.78 (1H, d, J=7Hz), 2.82 (1H, d, J=6Hz), 3.19 (1H, d, J=8Hz), 3.24 (1H, d, J=6Hz), 3.54 (1H, m), 3.97 (1H, dd, J=6, 8Hz), 4.08 (1H, dd, J=6, 7Hz), 4.43 (1H, d, J=5Hz), 7.15 (1H, s), 7.93 (1H, s)

This compound was identical with the FR-900490 prepared by culturing Discosia sp. F-11809.

EXAMPLE 2

To a mixture of (2S,3R)-2-amino-3-[[(1S)-1-carboxy-2-(4-imidazolyl)ethyl]amino]butyric acid (700 mg) and triethylamine (1.29 ml) in a mixture of water (10 ml) and dioxane was added t-butoxycarbonyl-L-alanine N-hydroxysuccinimide ester and the mixture was stirred for 4 hours at room temperature. The solvent was evaporated in vacuo and the residue was dissolved in 75% aqueous trifluoroacetic acid (20 ml). The solution was stored overnight at room temperature and the solvent was evaporated in vacuo. The residue was subjected to a column of Dowex 50W x 8 (30 ml) and the column was washed with water. The elution was carried out with 2.8% aqueous ammonia. The object fractions were collected and evaporated in vacuo. The residue was subjected to a column of Whatman CM52 (150 ml) and the elution was carried out with pyridine-acetic acid buffer (0.01M–0.14M, pH 4.9). The object fractions were collected and evaporated in vacuo. The residue was dissolved in water and lyophilized to give (2S,3R)-2-[[(2S)-2-aminopropionyl]amino]-3-[[(1S)-1-carboxy-2-(4-imidazolyl)ethyl]amino]butyric acid (580 mg).

mp: 155°–157° C. (dec.)

NMR (D$_2$O, δ): 1.14 (3H, d, J=7Hz), 1.23 (3H, d, J=6Hz), 3.27 (2H, m), 3.60 (1H, m), 3.9–4.3 (2H, m), 4.50 (1H, d, J=5Hz)

Mass (SIMS): m/z 328 (M$^+$+1)

EXAMPLE 3

To a mixture of 2S,3R)-2-amino-3-[[(1S)-1-carboxy-2-(4-imidazolyl)ethyl]amino]butyric acid (400 mg) and triethylamine (0.70 ml) in a mixture of water (10 ml) and dioxane (10 ml) was added (2S)-6-benzyloxycarbonylamino-2-t-butoxycarbonylaminohexanoic acid (894 mg) at 5° C. and the mixture was stirred in an ice-bath for 3 hours. The volatile solvent was evaporated in vacuo and the residue was adjusted to pH 4 with 1N hydrochloric acid. The mixture was subjected to a column of "Diaion HP-20" (80 ml). After the column was washed with water, the elution was carried out with a mixture of methanol and water (3:7–8:2) and the object fractions were collected and evaporated in vacuo. The residue was solidified with a mixture of methanol and ether to give (2S,3R)-2-[[(2S)-6-benzyloxycarbonylamino-2-t-butoxycarbonylaminohexanoyl]amino]-3-[[(1S)-1-carboxy-2-(4-imidazolyl)ethyl]amino]butyric acid (786 mg) as a white powder.

NMR (D$_2$O, δ): 1.26 (3H, d, J=7Hz), 1.3–1.8 (6H, m), 1.41 (9H, s), 3.0–3.3 (2H, m), 3.45 (2H, d, J=7Hz), 3.70 (1H, m), 3.9–4.3 (2H, m), 4.50 (1H, d, J=5Hz), 5.09 (2H, s), 7.38 (5H, s), 7.41 (1H, s), 8.62 (1H, s)

EXAMPLE 4

To a mixture of (2S,3R)-2-amino-3-[[(1S)-1-carboxy-2-(3-indolyl)ethyl]amino]butyric acid (207 mg) and triethylamine (0.33 ml) in a mixture of water (2 ml) and dioxane (5 ml) was added (2S)-2-benzyloxycarbonylamino-3-[N-[bis(4-methoxyphenyl)methyl]carbamoyl]propionic acid N-hydroxysuccinimide ester (560 mg) at 5° C. and the mixture was stirred in an ice-bath for 2 hours. The volatile solvent was evaporated in vacuo and the residual solution was adjusted to pH 4 with 1N hydrochloric acid. The precipitate was collected by filtration to give (2S,3R)-2-[[(2S)-2-benzyloxycarbonylamino-3-[N-[bis(4-methoxyphenyl)methyl]carbamoyl]propionyl]amino]-3-[[(1S)-1-carboxy-2-(3-indolyl)ethyl]amino]butyric acid (726 mg) as a white powder.

EXAMPLE 5

To a mixture of (2R,3S)-2-amino-3-[[(1S)-1-carboxy-2-(4-imidazolyl)ethyl]amino]butyric acid (200 mg) and triethylamine (0.38 ml) in a mixture of water (1.5 ml) and dioxane (5 ml) was added (2S)-2-benzyloxycarbonylamino-3-[N-[bis(4-methoxyphenyl)methyl]carbamoyl]propionic acid N-hydroxysuccinimide ester (586 mg) and the solution was stirred overnight at room temperature. The volatile solvent was removed in vacuo and the residual aqueous solution was adjusted to pH 4 with 1N hydrochloric acid. The precipitate was collected by filtration and dried in vacuo to give (2R,3S)-2-[[(2S)-2-benzyloxycarbonylamino-3-[N-[bis(4-methoxyphenyl)methyl]carbamoyl]propionyl]amino]-3-[[(1S)-1-carboxy-2-(4-imidazolyl)ethyl]amino]butyric acid (685 mg) as a white powder.

EXAMPLE 6

To a mixture of (2S)-2-amino-3-[[(1S)-1-carboxy-2-(4-imidazolyl)ethyl]amino]propionic acid (265 mg) and triethylamine (0.53 ml) in a mixture of water (4 ml) and dioxane (8 ml) was added (2S)-2-benzyloxycarbonylamino-3-[N-[bis(4-methoxyphenyl)methyl]carbamoyl]propionic acid N-hydroxysuccinimide ester (771 mg) in an ice-water bath. The mixture was stirred for 3.5 hours at ambient temperature and evaporated in vacuo to give a white residue, to which water (40 ml) was added. The suspension was adjusted to pH 3–4 with 6N hydrochloric acid in an ice-water bath. The precipitate was collected, washed with water (60 ml) and dried under reduced pressure to give a white powder (772 mg) of (2S)-2-[[(2S)-2-benzyloxycarbonylamino-3-[N-[bis(4-methoxyphenyl)methyl]-carbamoyl]propionyl]amino]-3-[[(1S)-1-carboxy-2-(4-imidazolyl)ethyl]amino]propionic acid.

EXAMPLE 7

The following compounds were obtained according to similar manners to those of Examples 4-6.
(1) (2S,3R)-2-[[(2S)-2-Benzyloxycarbonylamino-3-[N-[bis(4-methoxyphenyl)methyl]carbamoyl]propionyl]amino]-3-[[(1R)-1-carboxy-2-(4-imidazolyl)ethyl]amino]butyric acid
(2) Methyl (2S,3R)-2-[[(2S)-2-benzyloxycarbonylamino-3-[N-[bis(4-methoxyphenyl)methyl]carbamoyl]propionyl]amino]-3-[[2-(4-imidazolyl)ethyl]amino]butyrate
(3) 2S,3R)-2-[[(2R)-2-Benzyloxycarbonylamino-3-[N-[bis(4-methoxyphenyl)methyl]carbamoyl]propionyl]amino]-3-[[(1S)-1-carboxy-2-(4-imidazolyl)ethyl]amino]butyric acid
(4) (2S,3R)-2- [[(2S)-2-Benzyloxycarbonylamino-3-[N-[bis(4-methoxyphenyl)methyl]carbamoyl]propionyl]amino]-3-[[(1S)-1-carboxy-2-(4-hydroxyphenyl)ethyl]amino]butyric acid
(5) (2S,3R)-2-[[(2S)-2-Benzyloxycarbonylamino-3-[N-[bis(4-methoxyphenyl)methyl]carbamoyl]propionyl]amino]-3-carboxymethylaminobutyric acid

EXAMPLE 8

A solution of (2S,3R)-2-[[(2S)-2-benzyloxycarbonylamino-3-[N-[bis(4-methoxyphenyl)methyl]carbamoyl]propionyl]amino]-3-[[(1S)-1-carboxy-2-(3-indolyl)ethyl]amino]butyric acid (800 mg) in acetic acid (20 ml) was hydrogenated under medium pressure (3 atm.) for 8 hours at room temperature in the presence of 10% palladium on carbon (120 mg). After removal of the catalyst, the solution was evaporated in vacuo and the residue was solidified with water to give (2S,3R)-2-[[(2S)-2-amino-3-[N-[bis(4-methoxyphenyl)methyl]carbamoyl]propionyl]amino]-3-[[(1S)-1-carboxy-2-(3-indolyl)ethyl]amino]butyric acid (460 mg) as a yellow brown powder.

EXAMPLE 9

A solution of (2S,3R)-2-[[(2S)-6-benzyloxycarbonylamino-2-t-butoxycarbonylaminohexanoyl]amino]-3-[[(1S)-1-carboxy-2 (4-imidazolyl)ethyl]amino]butyric acid (720 mg) and 30% hydrogen bromide in acetic acid (20 ml) was sitrred for 3 hours at room temperature and the mixture was poured into ice-water (40 ml). The aqueous solution was washed with ether and subjected to a column of Dowex 50W x 8 (H+, 15 ml). The column was washed with water and the elution was carried out with 2.8% aqueous ammonia. The object fractions were collected and evaporated in vacuo. The residue was dissolved in water and lyophilized to give (2S,3R)-2-[[(2S)-2,6-diaminohexanoyl]amino]-3-[[(1S)-1-carboxy-2-(4-imidazolyl)ethyl]amino]butyric acid (399 mg) as a pale yellow powder.
mp: 175°-179° C.
Mass (SIMS): m/z 385 (M+ +1)
NMR (D$_2$O, δ): 1.10 (3H, d, J=7Hz), 1.3-2.0 (6H, m), 2.8-3.4 (5H, m), 3.6-3.8 (2H, m), 4.55 (2H, d, J=7Hz), 7.06 (1H, s), 7.83 (1H, s)

EXAMPLE 10

A solution of (2R,3S)-2-[[(2S)-2-benzyloxycarbonylamino-3-[N-[bis(4-methoxyphenyl)methyl]carbamoyl]propionyl]amino]-3-[[(1S)-1-carboxy-2-(4-imidazolyl)ethyl]amino]butyric acid (635 mg) and 30% hydrogen bromide in acetic acid (5 ml) was stirred for 2 hours at room temperature and the mixture was poured into a mixture of ice-water (20 ml) and ethyl acetate (20 ml). The aqueous phase was separated and subjected to a column of Dowex 50W x 8 (H+, 20 ml). The column was washed with water and the elution was carried out with 2.8% aqueous ammonia. The object fractions were collected and evaporated in vacuo. The residue was dissolved in water (50 ml) and lyophilized to give (2R,3S)-2-[[(2S)-2-amino-3-carbamoylpropionyl]amino]-3-[[(1S)-1-carboxy-2-(4-imidazolyl)ethyl]amino]butyric acid (190 mg) as a white powder.
mp: 120°-123° C. (dec.)
Mass (SIMS): m/z 371 (M+ +1)
NMR ( D$_2$O, δ): 1.63 (3H, d, J=7Hz), 2.87 (2H, d, J=7Hz), 3.0-3.3 (2H, m), 3.43 (1H, m), 3.9-4.4 (2H, m), 4.45 (1H, d, J=4Hz), 7.21 (1H, s), 8.07 (1H, s)

EXAMPLE 11

A solution of 30% hydrogen bromide in acetic acid (4.0 ml) was added to (2S)-2-[[(2S)-2-benzyloxycarbonylamino-3-[N-[bis(4-methoxyphenyl)methyl]carbamoyl]propionyl]amino]-3-[[(1S)-1-carboxy-2-(4-imidazolyl)ethyl]amino]propionic acid (772 mg) in an ice-water bath. The mixture was stirred for 15 minutes and then additional portion (4.0 ml) of a solution of hydrogen bromide in acetic acid was added thereto at ambient temperature. The mixture was stirred for 2.5 hours, and poured into a mixture of ice-water (25 ml) and ethyl acetate (25 ml). The aqueous layer was separated and then the remaining organic layer was extracted with water (30 ml). The aqueous layer were combined and subjected to a column of Dowex 50W x 8 (H$^{30}$ , 20 ml) and the elution was carried out with water (200 ml) and 1.4% aqueous ammonia (250 ml). The fractions containing the object compound were combined and evaporated in vacuo. The residue was dissolved in water (30 ml) and filtered. The filtrate was lyophilized to give a white powder (315 mg) of (2S)-2-[[(2S)-2-amino-3-carbamoylpropionyl]amino]-3-[[(1S)-1-carboxy-2-(4-imidazolyl)ethyl]amino]propionic acid.
NMR (D$_2$O, δ): 8.05 (1H, s), 7.19 (1H, s), 3.7-4.6 (3H, m), 2.7-3.4 (6H, m)
Mass (SIMS): m/z 357 (M+ +1)

EXAMPLE 12

The following compounds were obtained according to similar manners to those of Examples 10 and 11.
(1) (2S,3R)-2-[[(2S)-2-Amino-3-carbamoylpropionyl]amino]-3-[[(1R)-1-carboxy-2-(4-imidazolyl)ethyl]amino]butyric acid
mp : 171°-173° C.
NMR (D$_2$O, δ): 1.26 (3H, d, J=7Hz), 2.8-3.0 (2H, m), 3.0-3.3 (2H, m), 3.47 (1H, m), 3.9-4.3 (2H, m), 4.38 (1H, d, J=4Hz), 7.20 (1H, s), 8.04 (1H, s)
Mass (SIMS): m/z 371 (M+ +1)
(2) (2S,3R)-2-[[(2S)-2-Amino-3-carbamoylpropionyl]amino]-3-[[2-(4-imidazolyl)ethyl]amino]butyric acid
mp: 110°-114° C. (dec.)
NMR (D$_2$O, δ): 1.26 (3H, d, J=7Hz), 2.70 (2H, m), 2.8-3.3 (3H, m), 3.4-3.7 (2H, m), 3.92 (1H, m), 4.51 (1H, d, J=4Hz), 7.11 (1H, s), 7.80 (1H, s)

Mass (SIMS): m/z 327 (M+ +1)

(3) (2S,3R)-2-[[(2R)-2-Amino-3-carbamoylpropionyl]amino]-3-[[(1S)-1-carboxy-2-(4-imidazolyl)ethyl]amino]butyric acid mp: 181°–185° C.

NMR (D$_2$O, δ): 1.15 (3H, d, J=7Hz), 2.90 (2H, d, J=6Hz), 3.24 (2H, m), 3.50 (1H, dd, J=6, 5Hz), 4.01 (1H, dd, J=6, 7Hz), 4.28 (1H, t, J=7Hz), 4.52 (1H, d, J=5Hz), 7.19 (1H, s), 8.04 (1H, s)

Mass (SIMS): m/z 371 (M+ +1)

(4) (2S,3R)-2-[[(2S)-2-Amino-3-carbamoylpropionyl]amino]-3-[[(1S)-1-carboxy-2-(4-hydroxyphenyl)ethyl]amino]butyric acid mp: 170°–173° C. (dec.)

NMR (D$_2$O, δ): 1.11 (3H, d, J=7Hz), 2.8–3.0 (3H, m), 3.20 (1H, m), 3.53 (1H, m), 4.00 (1H, m), 4.24 (1H, dd, J=6, 8Hz), 4.47 (1H, d, J=5Hz), 6.93 (2H, d, J=8Hz), 7.26 (1H, d, J=8Hz)

Mass (SIMS): m/z 397 (M+ +1)

(5) (2S,3R)-2-[[(2S)-2-Amino-3-carbamoylpropionyl]amino]-3-carboxymethylaminobutyric acid mp: 146°–150° C.

NMR (D$_2$O, δ): 1.33 (3H, d, J=7Hz), 2.7–3.0 (2H, m), 3.40 (2H, s), 4.03 (1H, dd, J=5, 7Hz), 4.28 (1H, m), 4.55 (1H, d, J=5Hz)

Mass (SIMS): m/z 291 (M+ +1)

EXAMPLE 13

A solution of methyl (2S,3R)-2-[[(2S)-2-benzyloxycarbonylamino-3-[N-[bis(4-methoxyphenyl)methyl]carbamoyl]propionyl]amino]-3-[[2-(4-imidazolyl)ethyl]amino]butyrate (1.40 g) in a mixture of methanol (50 ml) and 1N aqueous sodium hydroxide (25 ml) was stirred for 30 minutes at room temperature and the mixture was adjusted to pH 7 with 1N hydrochloric acid. The precipitate was collected by filtration to give (2S,3R)-2-[[(2S)-2-benzyloxycarbonylamino-3-[N-[bis(4-methoxyphenyl)methyl]carbamoyl]propionyl]amino]-3-[[2-(4-imidazolyl)ethyl]amino]butyric acid (1.16 g) as a white powder.

EXAMPLE 14

A solution of (2S,3R)-2-[[(2S)-2-amino-3-[N-[bis(4-methoxyphenyl)methyl]carbamoyl]propionyl]amino] 3-[[(1S)-1-carboxy-2-(3 indolyl)ethyl]amino]butyric acid (427 mg) in a mixture of trifluoroacetic acid (3 ml), anisol (0.5 ml) and ethanedithiol (0.1 ml) was stirred overnight at room temperature and the mixture was poured into a mixture of water (10 ml) and ethyl acetate (10 ml). The aqueous phase was separated and subjected to a column of Dowex 50W x 8 (H+, 20 ml). The column was washed with water and the elution was carried out with 2.8% aqueous ammonia. The object fractions were collected and evaporated in vacuo. To the residue was added water and the mixture was lyophilized to give (2S,3R)-2-[[(2S)-2-amino-3-carbamoylpropionyl]amino]3-[[(1S)-1-carboxy-2-(3-indolyl)ethyl]amino]butyric acid (85 mg) as a pale brown powder.

mp: 65°–70° C.

Mass (SIMS): m/z 420 (M+ +1)

NMR (D$_2$O, δ): 0.90 (3H, d, J=6Hz), 2.6–2.9 (3H, m), 3.50 (1H, m), 3.9–4.3 (3H, m), 4.35 (1H, d, J=4Hz), 7.2–7.9 (5H, m)

PREPARATION 10

(1) A solution of methyl (2S)-1-tosyl-2-aziridinecarboxylate (1.04 g) in methanol was added to 1N aqueous sodium hydroxide (4.1 ml) in an ice bath and the mixture was stirred for 50 minutes at the same temperature. To the resulting solution were added L-histidine (2.11 g) and sodium hydroxide (730 mg) and the mixture was refluxed for 1.5 hours. After removal of the solvent in vacuo, the residue was dissolved in water and adjusted to pH 4 with 2N sulfuric acid. The solution was subjected to a column of "Diaion HP-20" (150 ml) and the column was washed with water. The elution was carried out with a mixture of water and methanol (1:1 400 ml). The eluate was evaporated in vacuo and the residue was chromatographed on a silica gel (100 g) column with a mixutre of chloroform, methanol and 28% aqueous ammonia (5:3:1) as an eluent to give (2S)-3-[[(1S)-1-carboxy-2-(4-imidazolyl)ethyl]amino]-2-tosylaminopropionic acid (485 mg).

NMR (D$_2$O-NaOD, δ): 2.21 (3H, s), 1.7–2.1 (4H, m), 3.44 (1H, t, J=6Hz), 3.74 (1H, dd, J=4,9Hz), 6.86 (1H, s), 7.41 (2H, d, J=9Hz), 7.74 (2H, d, J=9Hz) 7.84 (1H, s)

(2) (2S)-3-[[(1S)-1-carboxy-2- (4-imidazolyl ethyl]amino]-2-tosylaminopropionic acid (450 mg) was treated according to a similar manner to that of Preparation 9(2) to give (2S)-2-amino-3-[[(1S)-1-carboxy-2-(4-imidazolyl)ethyl]amino]propionic acid (265 mg).

mp: 215°–220° C. (dec.)

NMR (D$_2$O, δ): 3.0–3.2 (4H, m), 3.52 (1H, t, J=6.5Hz), 3.82 (1H, dd, J=5.5, 6.5Hz), 7.26 (1H, s), 8.47 (1H, s)

EXAMPLE 15

To a mixture of (2S, 3R)-2-[[(2S)-2-amino-3-carbamoylpropionyl] amino]-3-[[(1S)-1-carboxy-2-(4imidazolyl)ethyl]amino]butyric acid (500 mg) and triethylamine (0.38 ml) in a mixture of methanol(30 ml) and water (6 ml) was added acetic anhydride (0.13 ml) and the mixture was stirred for 20 hours at room temperature After removal of the solvent in vacuo, the residue was dissolved in water and adjusted to pH 3 with 1N hydrochloric acid. The solution was subjected to a column of Dowex 50W X 8 (H+ form, 10 ml) and the column was washed with water. The elution was carried out with 2% aqueous ammonia. The object fractions were collected and evaporated in vacuo and the residue was dissolved in a mixture of acetic acid (28.6 ml) and water (500 ml). The solution was lyophilized and the residue was solidified with methanol to give (2S, 3R)-2-[[(2S)-2-acetylamino-3-carbamoylpropionyl]amino]-3-[[(1S)-1-carboxy-2-(4-imidazolyl)ethyl]amino]butyric acid (500 mg).

mp: 205°–208° C. (dec.)

NMR (D$_2$O, δ): 1.24 (3H, d, J=6Hz), 2.05 (3H, s), 2.7–2.9 (2H, m), 3.4–3.5 (3H, m), 3.68 (1H, m), 4.12 (1H, m), 4.50 (1H, d, J=4Hz), 7.38 (1H, s), 8.55 (1H, s)

Mass (SIMS): m/z 413 (M+ +1)

PREPARATION 11

To a solution of pyridine (11.2 ml) in methylene chloride (300 ml) was added chromium trioxide (7.32 g) at 10°–15° C. After stirring for 1 hour at room temperature, the solution was cooled to 8° C. and a solution of N-(t-butoxycarbonyl)ethanolamine (2.0 g) in methylene chloride (20 ml) was added dropwise thereto. The mixture was stirred at the same temperature for 3 hours and the solution was filtered through Celite. The filtrate was evaporated in vacuo to give brown oil.

To a solution of the oil in methanol (46 ml) were added sodium bicarbonate (2.11 g), methyl (2S)-2-amino-3-(4-imidazolyl)propionate dihydrochloride (4.54 g) and sodium cyanoborohydride (833 mg) and the mixture was stirred overnight at room temperature. To the mixture was added a solution of sodium bicarbonate (3.15 g) in water (50 ml) and the solution was extracted with chloroform (100 ml). The organic phase was washed with brine and dried over magnesium sulfate. The solvent was evaporated in vacuo and the residue was chromatographed on a silica gel (50 g) with a mixture of chloroform and methanol (10:1) as an eluent to give N-(t-butoxycarbonyl)-2-[[(1S)-1-methoxycarbonyl-2-(4imidazolyl)ethyl]amino]ethylamine (757 mg) as a pale yellow oil.

NMR (CDCl$_3$, δ): 2.62 (2H, m), 2.86 (2H, m), 3.20 (2H, m), 3.53 (1H, m), 3.72 (3H, s), 6.83 (1H, s), 7.57 (1H, s)

PREPARATION 12

N-(t-Butoxycarbonyl)-2-[[(1S)-1-methoxycarbonyl-2-(4-imidazolyl)ethyl]amino]ethylamine (750 mg) was dissolved in a mixture of methanol (10 ml), water (5 ml) and trifluoroacetic acid (5 ml) and the solution was stirred for 2 hours at room temperature. After the removal of the solvent, the residue was dissolved in water (5 ml) and the solution was adjusted to pH 7 with 1N sodium hydroxide.

To the solution was added additional 1N sodium hydroxide (8 ml) and the mixture was stirred for 24 hours at room temperature. The resulting solution was adjusted to pH 3 with 1N hydrochloric acid and subjected to a column of Dowex 50W x 8 (20 ml). The column was washed with water and the elution was carried out with 2.8% aqueous ammonia. The object fractions were collected and evaporated in vacuo to give 2-[[(1S)-1-carboxy-2-(4-imidazolyl)ethyl]amino]ethylamine (448 mg).

NMR (D$_2$O, δ): 2.75 (1H, t, J=6.5 Hz), 2.8–3.0 (2H, m), 3.28 (1H, t, J=5 Hz), 3.37 (1H, t, J=6.5 Hz)

EXAMPLE 16

The following compounds were obtained according to similar manners to those of Examples 4–6.
(1) N-[(2S)-2-Benzyloxycarbonylamino-3-[N-[bis(4-methoxyphenly)methyl]carbamoyl]propionyl]-2-[[(1S)-1-carboxy-2-(4-imidazolyl)ethyl]amino]ethylamine
(2) (2S,3R)-3-[[(1S)-1-Carboxy-2-(4-imidazolyl)ethylamino]-2-[[3-[N-[bis(4-methoxyphenyl)methyl]-carbamoyl]propionyl]amino]butyric acid

EXAMPLE 17

The following compounds were obtained according to similar manners to those of Examples 10 and 11.
(1) N-[(2S)-2-Amino-3-carbamoylpropionyl]-2-[[(1S)-1-carboxy-2-(4-imidazolyl)ethyl]amino]ethylamine
mp: 105°–111° C. (dec.)

NMR (D$_2$O, δ): 2.66 (2H, t, J=5 Hz), 2.90 (1H, dd, J=4, 7.5Hz), 3.05–3.20 (2H, m), 3.53 (2H, t, J=5Hz), 3.82 (2H, m), 4.03 (1H, dd, J=4, 7.5Hz) 7.04 (1H, s), 7.85 (1H, s)
(2) (2S,3R)-2-[[3-Carbamoylpropionyl]amino]-3-[[(1S)-1-carboxy-2-(4-imidazolyl)ethyl]amino]butyric acid
mp: 130°–137° C. (dec.)

NMR (D$_2$O, δ): 1.11 (1H, d, J=7Hz), 2.5–2.8 (4H, m), 3.1–3.4 (2H, m), 4.07 (1H, t, J=6 Hz), 4.50 (1H, d, J=5Hz), 7.30 (1H, s), 8.24 (1H, s)

EXAMPLE 18

A seed medium (80 ml) (adjusted to pH 6.0) containing soluble starch (1%), corn starch (1%), glucose (1%), cotton seed meal (0.5%), dried yeast (0.5%), corn steep liquor (0.5%) and calcium carbonate (0.2%) was poured into each of thirty 250 ml Erlenmeyer flasks and sterilized at 120° C. for 30 minutes. A loopful of slant culture of Discosia sp. F-11809 was inoculated to each of the mediums and cultured at 25° C. for 72 hours on a rotary shaker with 3-inch throw at 200 rpm.

Twenty-four hundred milliliters of the seed culture were inoculated to the production medium (160 ) containing the same composition as that of seed medium in a 200 liter-jar fermentor, which had been sterilized at 120° C. for 30 minutes in advance, and cultured at 30° C. for 96 hours under aeration of 160 liters/minute and agitation of 300 rpm.

The cultured broth thus obtained was filtered with an aid of diatomaceous earth (4 kg). The filtrate was passed through an active carbon column (30 l). The column was washed with deionized water (90 l) and the elution was carried out with 60% aqueous acetone (90 l). The eluate was concentrated in vacuo to a volume of 60 liters and passed through a column of Dowex 50W-X2 (trademark, made by Dow Chemicals, H$^+$ type, 6 l). The column was washed with deionized water and the elution was carried out with 1.5% ammonia water (18 l). The eluate was concentrated in vacuo to dryness and then subjected to column chromatography on silica gel [Kieselgel 60, trademark, made by Merk & Co., 70–230 mesh, 1.8 l].

The column was washed with 80% aqueous isopropyl alcohol (1.8 l) containing 0.28% ammonia and 75% aqueous isopropyl alcohol (1.8 l) containing 0.28% ammonia, and then the elution was carried out 70% aqueous isopropyl alcohol containing 0.28% ammonia. The active fractions (2.5 () were concentrated in vacuo to a volume of 100 ml and then subjected to column chromatography on silica gel [Kieselgel 60, 70–230 mesh, 900 ml].

The column was washed with a mixture (1.8 l) of n-butyl alcohol, acetic acid and deionized water (3:1:2), and the elution was carried out with a mixture (1.8 l) of n-butyl alcohol, acetic acid and deionized water (2:1:2). The active fractions were neutralized with 6N aqueous sodium hydroxide and concentrated in vacuo to a volume of 100 ml. This solution was subjected to column chromatography on silica gel (600 ml). The elution was carried out with a mixture of n-butyl alcohol, ethyl alcohol, chloroform and 28% ammonia water (2:2:1:2). The active fractions (700 ml) were concentrated in vacuo to a volume of 400 ml and then passed through an active carbon column. The column was washed with deionized water (400 ml) and the elution was carried out with 60% aqueous acetone (400 ml). The eluate was concentrated to a volume of 30 ml and lyophilized to give 1.5 g of white powder of FR-900490.

What we claim is:

1. A compound of the formula:

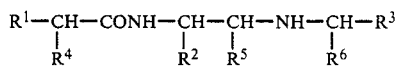

wherein

R$^1$ is amino or a protected amino group, $R^2$ is hydrogen, carboxy or a protected carboxy group, $R^3$ is hydrogen, carboxy or a protected carboxy group, $R^4$ is lower alkyl, amino(lower)alkyl, protected amino(lower)alkyl,, carbamoyl(lower)alkyl or protected carbamoyl(lower)alkyl, $R^5$ is hydrogen or lower alkyl, and $R^6$ is hydrogen, hydroxyphenyl(lower)alkyl, imidazolyl(lower)alkyl or indolyl(lower)alkyl, and pharmaceutically acceptable salts thereof.

2. A compound of claim 1, wherein $R^1$ is amino or acylamino, $R^2$ is hydrogen, carboxy or an esterified carboxy group, $R^3$ is hydrogen, carboxy or an esterified carboxy group, $R^4$ is lower alkyl, amino(lower)alkyl, acylamino(lower)alkyl, carbamoyl(lower)alkyl or [bix(4-methoxyphenyl)methyl]carbamoyl(lower)alkyl and, $R^5$ is hydrogen or lower alkyl.

3. A compound of claim 2, wherein $R^1$ is amino, lower alkoxycarbonylamino, ar(lower)alkoxycarbonylamino or lower alkanoylamino, $R^2$ is hydrogen, carboxy or lower alkoxycarbonyl, $R^3$ is hydrogen or carboxy, and $R^4$ is lower alkyl, amino(lower)alkyl, ar(lower)alkoxycarbonylamino(lower)alkyl, carbamoyl(lower)alkyl or [bis(4-methoxyphenyl)methyl]carbamoyl(lower)alkyl.

4. A compound of claim 1, wherein $R^6$ is imidazolyl(lower)alkyl.

5. A compound of claim 4, wherein $R^1$ is amino or acylamino, $R^2$ is hydrogen, carboxy or an esterified carboxy group, $R^3$ is hydrogen, carboxy or an esterified carboxy group, $R^4$ is lower alkyl, amino(lower)alkyl, acylamino(lower)alkyl, carbamoyl(lower)alkyl or [bis(4-methoxyphenyl)methyl]carbamoyl(lower)alkyl, and $R^5$ is hydrogen or lower alkyl.

6. A compound of claim 5, wherein $R^1$ is amino, lower alkoxycarbonylamino, ar(lower)alkoxycarbonylamino or lower alkanoylamino, $R^2$ is hydrogen, carboxy or lower alkoxycarbonyl, $R^3$ is hydrogen or carboxy, and $R^4$ is lower alkyl, amino(lower)alkyl, ar(lower)alkoxycarbonylamino(lower)alkyl, carbamoyl(lower)alkyl or [bis(4-methoxyphenyl)methyl]carbamoyl(lower)alkyl.

7. A compound of claim 6, wherein $R^1$ is amino, $R^2$ is carboxy, $R^3$ is carboxy, $R^4$ is carbamoyl(lower)alkyl, and $R^5$ is lower alkyl.

8. A compound of claim 7, which is (2S,3R)-2-[[(2S)-2-amino-3-carbamoylpropionyl]amino]-3-[[(1S)-1-carboxy-(2-4-imidazolyl)ethyl]amino]butyric acid.

9. A pharmaceutical composition comprising, as an effective ingredient, the compound of claim 1 and pharmaceutically acceptable carrier (s).

* * * * *